United States Patent
Song et al.

(10) Patent No.: US 9,245,359 B2
(45) Date of Patent: Jan. 26, 2016

(54) APPARATUS AND METHOD FOR GENERATING MEDICAL IMAGE USING LINEAR GAMMA RAY SOURCE

(71) Applicant: Samsung Electronics Co., Ltd., Suwon-si (KR)

(72) Inventors: Tae-yong Song, Hwaseong-si (KR); Byung-kwan Park, Seoul (KR); Jae-mock Yi, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 286 days.

(21) Appl. No.: 13/970,876

(22) Filed: Aug. 20, 2013

(65) Prior Publication Data

US 2014/0050380 A1 Feb. 20, 2014

(30) Foreign Application Priority Data

Aug. 20, 2012 (KR) ........................ 10-2012-0090899

(51) Int. Cl.
*G06K 9/00* (2006.01)
*G06T 11/00* (2006.01)
*A61B 6/03* (2006.01)

(52) U.S. Cl.
CPC ............... *G06T 11/003* (2013.01); *A61B 6/037* (2013.01)

(58) Field of Classification Search
None
See application file for complete search history.

(56) References Cited

U.S. PATENT DOCUMENTS

| 7,983,465 | B2 | 7/2011 | Leroux et al. |
| 8,958,622 | B2 * | 2/2015 | Vija et al. ...................... 382/131 |
| 2003/0178559 | A1 | 9/2003 | Hamill et al. |
| 2009/0008562 | A1 | 1/2009 | Grazioso et al. |
| 2009/0080790 | A1 * | 3/2009 | Hasegawa ...................... 382/260 |
| 2010/0067758 | A1 | 3/2010 | Casey et al. |
| 2013/0258313 | A1 * | 10/2013 | Orband .......................... 356/51 |
| 2014/0050380 | A1 * | 2/2014 | Song et al. ................... 382/131 |

FOREIGN PATENT DOCUMENTS

| JP | 2005-326406 | 11/2005 |
| KR | 10-2010-0117207 A | 11/2010 |

OTHER PUBLICATIONS

Panin, Vladimir Y. et al. "Fully 3-D PET Reconstruction With System Matrix Derived From Point Source Measurements", IEEE Transaction on Medical Imaging, vol. 25, No. 7, Jul. 2006, pp. 907-921 (15 pages, in English).

Ortuño, Juan E. et al. "3D-OSEM iterative image reconstruction for high-secolution PE using precalculated system matrix", Nuclear Instruments and Methods in Physic Research A 269 (2006) pp. 440-444 (5 pages, in English).

* cited by examiner

*Primary Examiner* — Tahmina Ansari
(74) *Attorney, Agent, or Firm* — NSIP Law

(57) ABSTRACT

Methods and apparatuses for generating a blur model of a detector, and methods and apparatus for generating a medical image are provided. A method of generating a blur model of a detector may involve: changing locations of linear gamma ray sources along at least one line and obtaining signals emitted from the linear gamma ray sources; obtaining a point spread function (PSF) with respect to at least one voxel included in the at least one line; and generating a blur model of the detector from the PSF.

24 Claims, 7 Drawing Sheets

APPARATUS AND METHOD FOR GENERATING MEDICAL IMAGE USING LINEAR GAMMA RAY SOURCE

CROSS-REFERENCE TO RELATED APPLICATIONS

This application claims the benefit under 35 U.S.C. §119(a) of Korean Patent Application No. 10-2012-0090899, filed on Aug. 20, 2012, in the Korean Intellectual Property Office, the entire disclosure of which is incorporated herein by reference for all purposes.

BACKGROUND

1. Field

The following description relates to methods and apparatuses for generating a medical image and to, for example, methods and apparatus of generating a positron emission tomography (PET) image by using a linear gamma ray source.

2. Description of Related Art

A medical image device is used to diagnose a patient by obtaining information about the patient via an image of the functional processes that are taking place inside the human body. Methods of capturing a medical image have actively been developed and are currently used in hospitals. Such methods are largely divided into methods of obtaining an anatomical image and methods of obtaining a physiological image. Examples of imaging technologies that provide a detailed, high resolution anatomical image of the human body include magnetic resonance imaging (MRI) and computed tomography (CT). In such an imaging technology, a 2-dimensional (2D) image of a cross-section of the human body or a 3D image of the human body or a part thereof is generated so as to show accurate locations and shapes of organs in the human body. The 3D image may be obtained by using several 2D high-resolution images. An example of technology for acquiring a physiological image includes positron emission tomography (PET). PET can be used to diagnose a metabolic disorder by obtaining an image of the metabolic processes that are take place inside the human body.

PET is an imaging technology in which special radioactive tracers that emit positrons are generated in the forms of components participating in the metabolic processes of the human body. The tracers are injected into the human body via an intravenous injection or inhalation, and the locations of the tracers are obtained by using an external device (a scanner) that detects two gamma rays of 511 eV emitted in opposite directions to each other when the positrons emitted from the tracers and electrons combine with each other. Both the pattern of distribution of the gamma rays and a change in the distribution pattern with respect to time may be observed.

In this regard, physiological phenomena that continue to occur inside the body during a process of detecting a gamma ray, a geometrical structure of a detector, spatial restrictions due to the shape and arrangement of detection elements in the detector, and the like, may adversely affect a spatial resolution of the PET, and may further influence the ability of a user to read and interpret a patient's image or deteriorate the disease diagnostic capability of the imaging device. Among such spatial resolution deterioration factors, it is in particular impossible to control the continued occurrence of physiological phenomena inside the body. Further, spatial restrictions may cause a design issue that is difficult to overcome with respect to the structure of the detector.

SUMMARY

In one general aspect, there is provided a method of generating a blur model of a detector, the method involving: changing locations of linear gamma ray sources along at least one line and obtaining signals emitted from the linear gamma ray sources; obtaining a point spread function (PSF) with respect to at least one voxel included in the at least one line; and generating a blur model of the detector from the PSF.

In the general aspect of the method, the obtaining of the PSF with respect to the at least one voxel may involve: generating a line spread function (LSF) with respect to the at least one line based on the obtained signals; and separating the LSF with respect to each of the at least one line into the PSF with respect to each of the at least one voxel.

In the general aspect of the method, the linear gamma ray sources may include a plurality of point gamma ray sources.

In the general aspect of the method, the plurality of point gamma ray sources may be spaced apart from each other by a uniform space.

In the general aspect of the method, the separating may involve fitting the LSF with respect to each of the at least one line to a sum of a plurality of functions, and each of the plurality of functions may be the PSF with respect to each of the at least one voxel.

In the general aspect of the method, the plurality of functions may be Gaussian functions.

The general aspect of the method may further involve: calculating a parameter for representing a function corresponding to the separated PSF, and the blur model of the detector may be generated from the parameter with respect to the at least one voxel.

In the general aspect of the method, the linear gamma ray sources may comprise at least two linear gamma ray sources that are disposed parallel to each other.

In another general aspect, there is provided a method of generating a medical image, the method involving: changing locations of linear gamma ray sources along at least one line and obtaining signals emitted from the linear gamma ray sources; obtaining a point spread function (PSF) with respect to at least one voxel included in the at least one line; generating a blur model of the detector from the PSF; generating a first image based on a signal emitted from a tracer; and generating a second image by applying the blur model to the first image.

In the general aspect of the method, the obtaining of the PSF with respect to the at least one voxel may involve: generating a line spread function (LSF) with respect to the at least one line based on the obtained signals; and separating the LSF with respect to each of the at least one line into the PSF with respect to each of the at least one voxel.

In the general aspect of the method, a resolution of the second image may be higher than that of the first image.

In the general aspect of the method, the generating of the second image may involve: using an expectation maximization (EM) algorithm.

In another general aspect, there is provided an apparatus for generating a blur model, the apparatus including: a signal obtaining unit for changing locations of linear gamma ray sources along a line and obtaining signals emitted from the linear gamma ray sources; a PSF obtaining unit for obtaining a point spread function (PSF) with respect to at least one voxel included in the at least one line; and a blur model generation unit for generating a blur model from the PSF.

In the general aspect of the apparatus, the PSF obtaining unit may include: a line spread function (LSF) generation unit for generating a LSF with respect to the least one line based on the obtained signals; and a separation unit for separating the LSF with respect to each of the at least one line into the PSF with respect to each of the at least one voxel.

In the general aspect of the apparatus, the linear gamma ray sources may include a plurality of point gamma ray sources.

In the general aspect of the apparatus, the plurality of point gamma ray sources may be spaced apart from each other by a uniform space.

In the general aspect of the apparatus, the separation unit may include a fitting unit for fitting the LSF with respect to each of the at least one line to a sum of a plurality of functions, and each of the plurality of functions may be the PSF with respect to each of the at least one voxel.

In the general aspect of the apparatus, the plurality of functions may be Gaussian functions.

The general aspect of the apparatus may further include: a parameter calculation unit for calculating a parameter for representing a function corresponding to the separated PSF, and the blur model generation unit may generate the blur model from the parameter with respect to the at least one voxel.

In the general aspect of the apparatus, the linear gamma ray sources may include at least two linear gamma ray sources that are disposed parallel to each other.

In another general aspect, there is provided an apparatus for generating a medical image. The apparatus may include: a signal obtaining unit for changing locations of linear gamma ray sources along at least one line and obtaining signals emitted from the linear gamma ray sources; a point spread function (PSF) obtaining unit for obtaining a PSF with respect to at least one voxel included in the at least one line; a blur model generation unit for generating a blur model from the PSF; a first image generation unit for generating a first image based on a signal emitted from a tracer; and a second image generation unit for generating a second image by applying the blur model to the first image.

In the general aspect of the apparatus, the PSF obtaining unit may include: a line spread function (LSF) generation unit for generating a LSF with respect to the least one line based on the obtained signals; and a separation unit for separating the LSF with respect to each of the at least one line into the PSF with respect to each of the at least one voxel.

In the general aspect of the apparatus, the second image generation unit may use an EM algorithm to generate the second image.

In yet another general aspect, there is provided a non-transitory computer-readable recording medium having recorded thereon a program for executing the general aspect of methods described above.

Other features and aspects may be apparent from the following detailed description, the drawings, and the claims.

Figure 1:
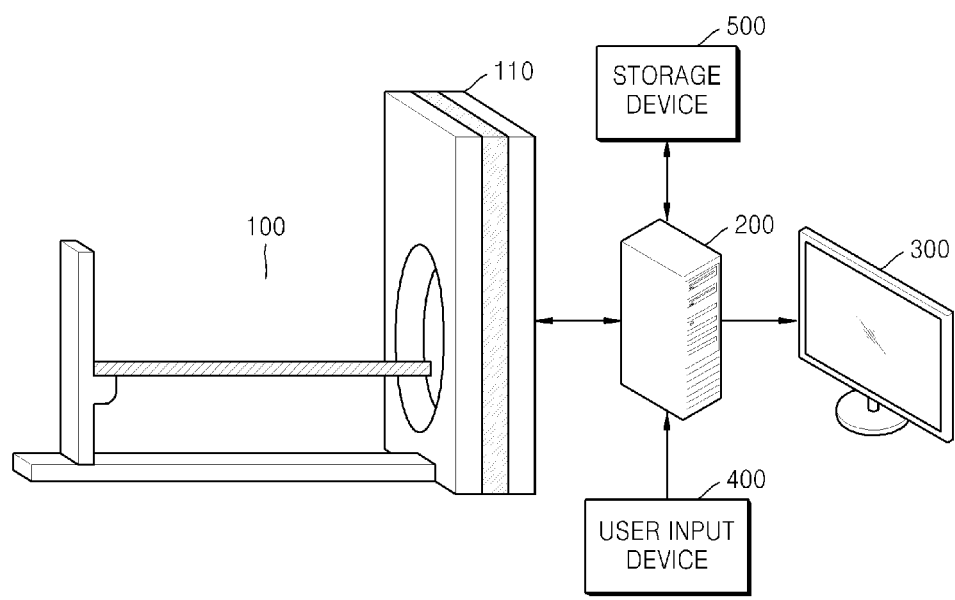
FIG. 1 a diagram illustrating an example of an apparatus for generating a medical image.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Described below are examples of methods and apparatuses for generating a high resolution positron emission tomography (PET) image by using a linear gamma ray source. Also described are a method of obtaining an image by placing a source for emitting the gamma ray inside a detector, discovering information about the blurring pattern indicating how the image is blurred by the detector, applying a system matrix reflecting the blur information to the image, and generating a clear image. Further described are examples of computer-readable recording media having recorded thereon a program for executing such methods.

FIG. 1 is a diagram illustrating an example of an apparatus for generating a medical image. FIG. 1 illustrates an overall system for generating an image of a cross-section of the body of a patient. Referring to FIG. 1, the apparatus includes a signal detection device 100, a computer 200, a display device 300, a user input device 400, and a storage device 500.

According to an example, the apparatus for generating the medical image of FIG. 1 may be used to generate an image of a physiological process taking place inside a patient along a cross-section of the body of the patient as well as to generate a blur model of a detector 110 to refine the generated image. The aspects of a method of generating the image of the physiological process of the body along a cross-section of the body of the patient and a method of generating the blur model of the detector 110 by using the apparatus for generating the medical image of FIG. 1 will now be described below.

In this regard, blurring represents a degree of spread of a point or an image. In an example, if a detector 110 is used to estimate locations of positron emission materials located in a detection space of the detector 110, the blurring relates how a distribution of the estimated locations spreads or how the estimated locations are smudged with respect to actual locations of the positron emission materials. A point spread function (PSF) may be used to represent such a degree of blurring.

In addition, a blur model of a detector 110 is a representation of the blur information of an image captured by the detector 110 in the PSF with respect to a voxel of the detector 110 or transformation of the PSF into a system matrix. A voxel refers to a location coordinate in a 3D space of the detector 110.

For example, in the event that an apparatus for generating the medical image is used to generate a blur model of a detector 110, the apparatus for generating the medical image obtains a signal from a positron emission material having a first location coordinate in a detection space of the detector 110, generates an image with respect to a first location, and generates a PSF indicating the blur information in the image. The PSF is a PSF with respect to the first location.

Next, the apparatus for generating the medical image changes the location of the positron emission material to a second location and generates a PSF with respect to the second location. Thus, PSFs with respect to a plurality of voxels including the first location and the second location in the detector 110 may be generated. The PSFs with respect to the plurality of voxels may be used to generate PSFs with respect to all voxels of a detection space of the detector 110. The PSFs with respect to all voxels may be used as a blur model of the detector 110. Furthermore, in a case in which a PET image is generated using the apparatus for generating the medical image, a clear and high resolution PET image from which the blurring has been eliminated may be obtained by applying the blur model to an image obtained from the detector 110.

For example, the apparatus for generating the medical image may capture an image of a cross-section of the body of a patient, and may apply the blur model of the detector 110 to the captured image, thereby obtaining a clear and high resolution PET image from which the blurring has been eliminated. The detailed operations will now be described with reference to various examples.

In this regard, a blur model is applied to the captured image in order to obtain a still image. The blur model is applied by deconvoluting a blur filter with respect to a blurry image, and/or by inversely using a principle of obtaining the blurry image by convoluting the blur filter with respect to the still image.

For example, in an example in which the apparatus for generating the medical image of FIG. 1 is used to generate a physiological image of a cross-section of the body of a patient, the signal detection device 100 of the FIG. 1 detects a signal emitted by a tracer injected into the body of the patient. In this example, the body of the patient is a target of the apparatus for generating a medical image. In this regard, the tracer is a positron emission material that is directly injected into the body of a patient who is the target of the PET imaging device. The tracer emits a gamma ray to the outside from an organ, blood vessel, tissue, and the like of the human body. The signal detection device 100 may, for example, detect two gamma rays that are emitted when a positron emitted from the tracer that has been injected into the body of a patient combines with an electron. When the positron and the electron collide, the positron annihilates and releases energy in the form of two gamma rays. The two gamma rays are two 511 keV photons traveling in opposite directions, and the direction that these photons travel defines a line of response (LOR) that may be detected by the detector 110. The signal detection device 100 transmits the line of response (LOR) data regarding the detected gamma rays to the computer 200.

For example, in the event that the apparatus for generating the medical image illustrated in FIG. 1 is used to generate a blur model of a detector 110, the signal detection device 100 of FIG. 1 may detect two gamma rays that are emitted when a positron emitted from a gamma ray source combines with an electron in the inner space of the detector 110. The signal detection device 100 may transmit LOR data regarding the detected gamma rays to the computer 200. In this regard, the source of the gamma line is a positron emission material that is injected into the body. The gamma line is produced when the positron emitted from the gamma ray source combines with an electron, and the gamma rays are detected by the detector 110.

The LOR data includes information regarding the location of a tracer. In this regard, LOR is a straight line in an inner space of the detector 110 through which two gamma rays travel after a positron and an electron annihilate. The LOR data will now be described below with reference to FIG. 2.

Figure 2:
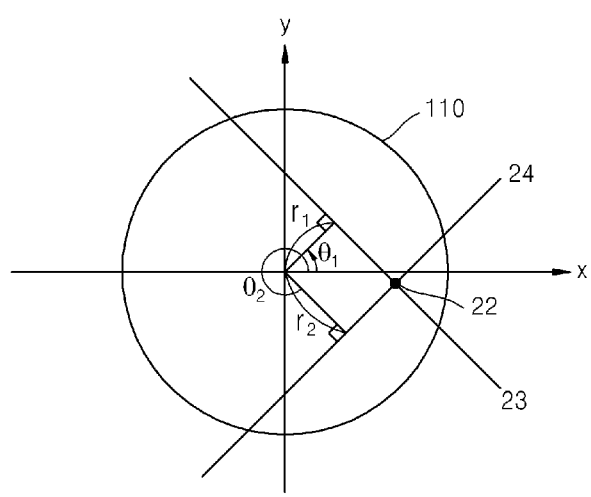
FIG. 2 is a diagram illustrating an example of a method of interpreting line of response (LOR) data.

FIG. 2 is a diagram for explaining the interpretation of an example of LOR data. Referring to FIG. 2, a tracer 22 located in a detecting space of the detector 110. The tracer 22 emits two gamma rays in two opposite directions or substantially opposite directions when positrons emitted from the tracer 22 react with electrons and annihilate. The two gamma rays are emitted in opposite directions that are approximately 180° from each other, forming a straight line. FIG. 2 illustrates two straight lines 23 and 24, which represent the paths of two sets of gamma rays emitted from positrons released from the tracer 22. Referring to the straight line 23, when a perpendicular line is drawn on the straight line 23 starting from an origin of the detecting space of the detector 110, a distance from the origin to the straight line 23 is r1 and an angle between the perpendicular line on the straight line 23 and an x-axis of the detecting space of the detector 110 is $\theta 1$. Thus, the LOR corresponding to the straight line 23 is (r1, $\theta 1$). Similarly, referring to the straight line 24, when a perpendicular line is drawn on the straight line 24 starting from the origin of the detecting space of the detector 110, a distance from the origin to the straight line 24 is r2 and an angle between the perpendicular line on the straight line 24 and the x-axis of the detecting space of the detector 110 is $\theta 2$. Thus, the LOR corresponding to the straight line 24 is (r2, $\theta 2$). As described above, when two or more pieces of LOR data are obtained, a location of the tracer 22 may be determined from the LOR data. Accordingly, the signal detection device 100 may transmit LOR data about detected gamma rays to the computer 200, and the computer 200 may finally determine a location of a tracer from the LOR data.

Referring back to FIG. 1, the computer 200 generates an image of the target by using data obtained from the signal detection device 100. For example, in the case where the physiological image of the cross-section of the body of the patient is generated, the computer 200 generates the physiological image from the cross-section of the body of the patient by using the data obtained from the signal detection device 100. For example, to generate a blur model of a detector 110, the computer 200 generates the blur model of the detector 110 by using the data obtained from the signal detection device 100.

The display device 300 may display the image generated from the computer 200 or the blur model on a display panel. The display device 300 may further display any information to be provided to a user.

The user may input information required for operations of the computer 200 by using the user input device 400. For example, the user may command to start and stop operations of the computer 200 by using the user input device 400.

With respect to the computer 200 that generates the PET image with respect to the target, the image quality may be influenced by a spatial resolution of the detector 110. Factors that deteriorate the spatial resolution in the PET may include an angle fluctuation of a gamma ray, a range of a positron, a geometrical structure of a detector, an algorithm accuracy detecting a gamma ray reaction location of the detector, and the like.

With respect to the angle fluctuation of the gamma ray, the resolution of the PET image deteriorates in the event that the two gamma rays emitted from a tracer do not precisely form 180 degrees. For example, the two gamma rays may form an angle that is slightly greater or less than 180 degrees. This example will now be described below with reference to FIG. 3.

Figure 3:
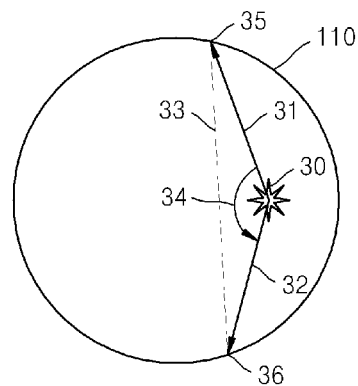
FIG. 3 is a diagram illustrating an example of two gamma rays emitted from a tracer that do not form a straight line.

FIG. 3 is a diagram for describing an example of two gamma rays 31 and 32 emitted from a tracer 30 that do not form a straight line.

FIG. 3 shows the example of the two gamma rays 31 and 32 emitted from the tracer 30 that do not precisely form 180 degrees. Rather, the two gamma rays 31 and 32 form an angle 34 that is slightly greater or less than 180 degrees. The angle 34 may be in a range of about 177.5 degrees to about 182.5 degrees, for example. In this example, the detector 110 recognizes locations 35 and 36 as the locations where the two gamma rays 31 and 32 are detected. Based on the detection locations 35 and 36, the detector may be configured to estimate that the tracer 30 is located on a straight line 33 that connects the locations 35 and 36. However, the tracer 30 does not actually exist on the straight line 33 between the locations 35 and 36. This type of error becomes more pronounce when the diameter of the detector 110 is large, significantly worsening the resolution of a PET image obtained by the detector 110.

In addition, with respect to the range of a positron, the resolution of the PET image deteriorates more as the positron moves further away from a tracer before it collides with an electron. A positron loses energy while moving a short distance after being emitted from the tracer. Thereafter, the positron collides into an electron and is annihilated. At this time, two gamma rays having energy of 511 keV are emitted in approximately 180 degrees from each other. The distance that the positron travels while losing its energy is referred to as a positron range. The positron only emits the two gamma rays after moving away from the tracer by the position range; thus, the actual location of the tracer and the location at which the two gamma rays are emitted are not precisely consistent with each other. Thus, if the location at which gamma rays are emitted is calculated and estimated to be the location of the tracer, an error occurs with respect to the true location of the tracer. The deterioration of the resolution of PET due to such an error is referred to as a positron range effect. In general, the greater the energy of the positron, the greater the positron range and the lower the resolution of the PET image.

For example, with respect to a geometrical structure of the detector 110, due to a parallax error, which results from the uncertainty of the depth of interaction (DOI) of the gamma rays, for each location in the geometrical structure of the detector 110, the farther from the center of the detector 110, the resolution of the PET image is lower. For example, a plurality of detection elements may be closely arranged on a surface of the detector 110. In the event that the detection elements have rectangular shapes that are longer in a depth direction, if a gamma ray is inclinedly incident on the detection elements, the gamma ray may be simultaneously detected in several adjacent detection elements rather than being detected in only one detection element. Thus, it becomes difficult to estimate a precise location of a tracer and the resolution of the PET deteriorates.

The resolution of the PET deteriorates due to various factors other than the above three factors. Some of these factors occur stochastically; thus, an enhancement of the resolution through a technical or mechanical design change is limited to a certain degree. Thus, to solve this restriction, a method of generating stochastic blur information corresponding to each voxel of the detecting space of the detector 110 in a form of a PSF, generating a blur model with respect to the detector 110 from the PSF, inversely applying the blur model of the detector 110 to a low resolution PET image captured by using the detector 110, and generating a high resolution image from which blur is eliminated is proposed.

According to another example, the apparatus for generating the medical image of FIG. 1 may be used in a method to generate a physiological image of a cross-section of a patient and to generate a blur model of a detector 110 that has been used to generate the physiological image. An example of a method of generating the blur model of the detector 110 by using the apparatus for generating the medical image will be described below with reference to FIGS. 4 through 6.

Figure 4:
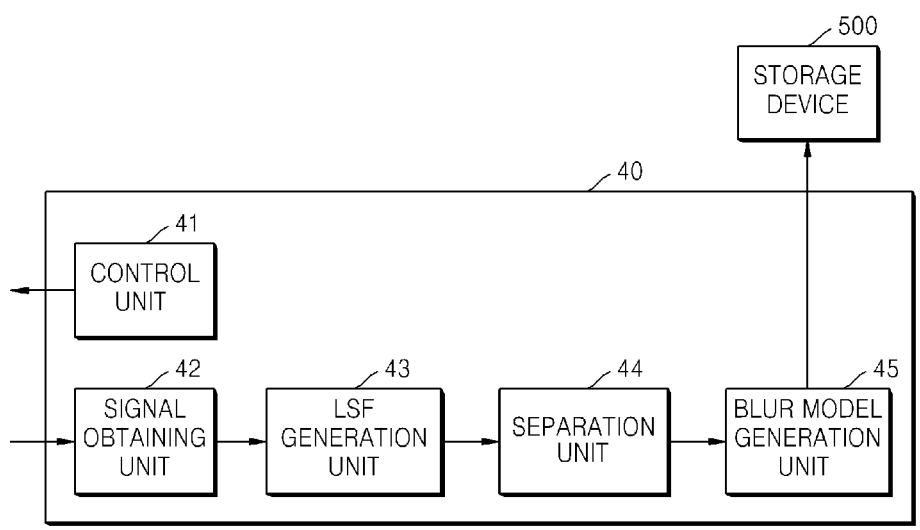
FIG. 4 is a partial block diagram illustrating an example of a blur model generating apparatus that generates a blur model.

FIG. 4 illustrates an example of a blur model generation device 40 that generates a blur model. In a example in which the apparatus for generating the medical image illustrated in FIG. 1 is used to generate the blur model of the detector 110, the computer 200 of FIG. 1 may include the blur model generation device 40 illustrated in FIG. 4. Referring to FIG. 4, the blur model generation device 40 includes a control unit 41, a signal obtaining unit 42, a line spread function (LSF) generation unit 43, a separation unit 44, and a blur model generation unit 45. The LSF generation unit 43 and the separation unit 44 may form a PSF obtaining unit 46 that is configured to obtain a PSF. The control unit 41, the signal obtaining unit 42, the LSF generation unit 43, the separation unit 44, and the blur model generation unit 45 may include one or more processors. A blur model generated by the blur model generation unit 45 may be stored in the storage device 500. The storage device 500 may be implemented as a part of the computer 200 illustrated in FIG. 1.

The control unit 41 changes locations of linear gamma ray sources in a detection space of a 3D detector 110. In this regard, the linear gamma ray sources comprise gamma ray sources that emit positrons and are arranged in a straight line. For example, the control unit 41 may change the locations of the linear gamma ray sources gradually in a direction away from the center of the detector 110.

In an example in which the detector 110 has a cylindrical shape, the control unit 41 may change the locations of the linear gamma ray sources in such a way that a length direction of the linear gamma ray sources is aligned with an axial direction of the detector 110. Accordingly, the control unit 41 may change the locations of the linear gamma ray sources in such a way that an angle from a predetermined plane crossing the center of the detector 110 to the linear gamma ray sources increases at a predetermined angle interval. In addition, to obtain signals with respect to various locations in the detector 110, the control unit 41 may change the locations of the linear gamma ray sources by using a variety of methods known to those skilled in the art.

Meanwhile, a point gamma ray source other than the linear gamma ray source may be used to generate the blur model. For example, the blur model generation device 40 may change locations of the point gamma ray sources on an x-y plane (perpendicular to a depth direction), and accordingly may generate a PSF with respect to voxels on a predetermined x-y plane. This process may be repeatedly performed in a z-axial direction, and accordingly a PSF with respect to voxels on a plurality of x-y planes may be generated. That is, the blur model generation device 40 may change the locations of the point gamma ray sources in all x-, y-, and z-axial directions, and accordingly may generate a PSF with respect to voxels of a 3D space.

However, it is inefficient to generate a PSF from a signal detected with respect to a location of each of point gamma ray sources in all locations of the detector 110 in terms of time or data capacity. A PET system actually has a large number of voxels. Thus, it is practically impossible to measure PSFs at all voxels. For example, in a case where voxels of a PET detection space are 336, 336, and 109, respectively, on a 3D coordinate axis, the total number of voxels is 336×336×109 or 12,305,664.

Accordingly, a method of calculating a PSF with respect to some voxels by placing the point gamma ray sources in some locations, estimating a PSF with respect to other voxels from the calculated PSF, and generating the blur model of the detector 110 is proposed. For example, a PSF corresponding to a total number of 1600 voxels may be generated by calculating a PSF with respect to 40 voxels for each plane and performing 40 repetitive measurements in an axial direction.

An example of the method of calculating a PSF with respect to some voxels and estimating a PSF with respect to other voxels from the calculated PSF is an interpolation method of estimating a PSF in a third location between a first location and a second location by giving a weight to a PSF of the first location and a PSF of the second location. For another example, in the case of different voxels having the same PSF or different voxels having diagonal PSFs, since a PSF with respect to other voxels may be estimated from a PSF with respect to one voxel, an operation of generating the PSF with respect to other voxels may be omitted.

An example of a method of calculating a PSF with respect to one voxel and estimating a PSF with respect to other voxels from the calculated PSF will now be explained below.

For example, it is assumed that an x-y plane of the detector 110 is a perfect circular shape, and accordingly, voxels having the same distance from the center of the detector 110 have the same PSF on a predetermined x-y plane of the detector 110. In this case, the blur model generation device 40 may generate a PSF with respect to the overall of the x-y plane by using a PSF with respect to a voxel that is "on the predetermined x-y plane and simultaneously is on a predetermined straight line crossing the center of the detector 110".

Alternatively, it is assumed that the x-y plane of the detector 110 is divided into a plurality of trapezoidal shapes, and a PSF with respect to each of the trapezoidal shapes is consistent with a rotation of a PSF with respect to different trapezoidal shapes with respect to the center of the x-y plane of the detector 110. In this case, the blur model generation device 40 may generate a PSF with respect to a first trapezoidal shape and generate a PSF with respect to the overall x-y plane by using the PSF with respect to the first trapezoidal shape.

An example of the control unit 41 that changes a location of a linear gamma ray source will be described below with reference to FIG. 8. Prior to this example, an example of changing a location of a point gamma ray source to compare the point gamma ray source with the linear gamma ray source will now be described below with reference to FIG. 6.

Figure 6:
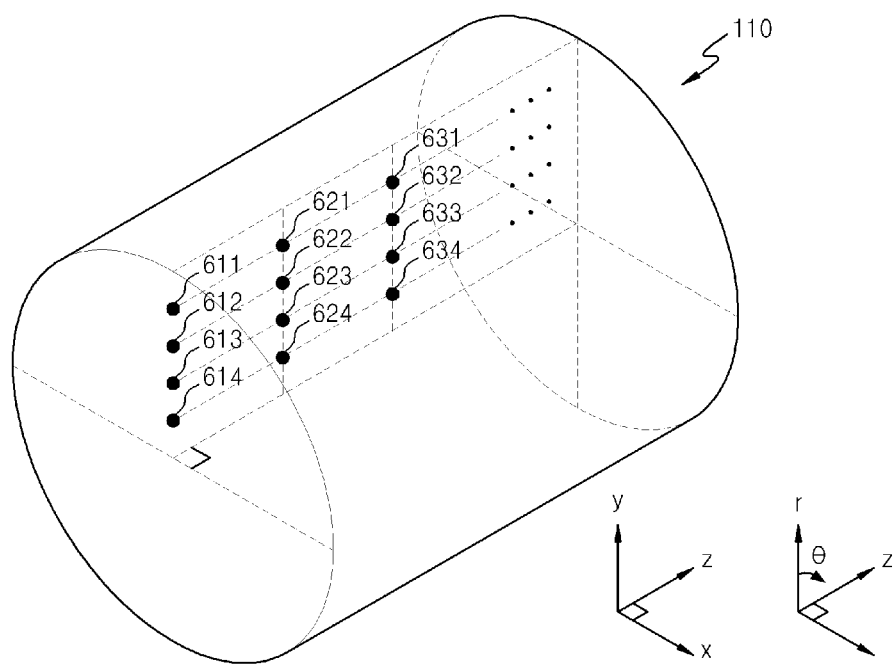
FIG. 6 is a diagram illustrating an example of changing locations of point gamma ray sources in a detection space of a detector.
Figure 7:
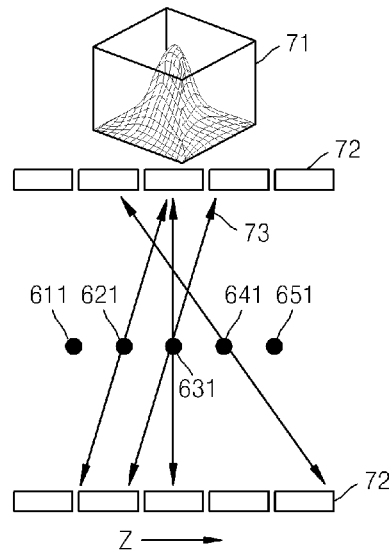
FIG. 7 is a diagram illustrating an example of generating a point spread function (PSF) using a signal obtained from a point gamma ray source.

FIG. 6 is a diagram for describing an example of changing location of point gamma ray sources in a detection space of the detector 110. Referring to FIG. 6, the locations of the point gamma ray sources may be changed to voxels 611, 612, 613, and 614 in the detection space of the detector 110. The voxel 611 to the voxel 614 indicate arbitrary voxels on a first plane that is an x-y plane including the voxel 611 to the voxel 614. The locations of the point gamma ray sources may be changed to other voxels on the first plane. Accordingly, the blur model generation device 40 generates a PSF with respect to the first plane by obtaining a signal from each location of the point gamma ray sources.

FIG. 7

The blur model generation device 40 repeatedly performs the above operation of generating a PSF with respect to a predetermined plane while moving the predetermined plane along a z-axis. Accordingly, the locations of the point gamma ray sources may be changed to voxels 621 to 624, and thereafter, to voxels 631 to 634 in a z-axial direction.

Figure 8:
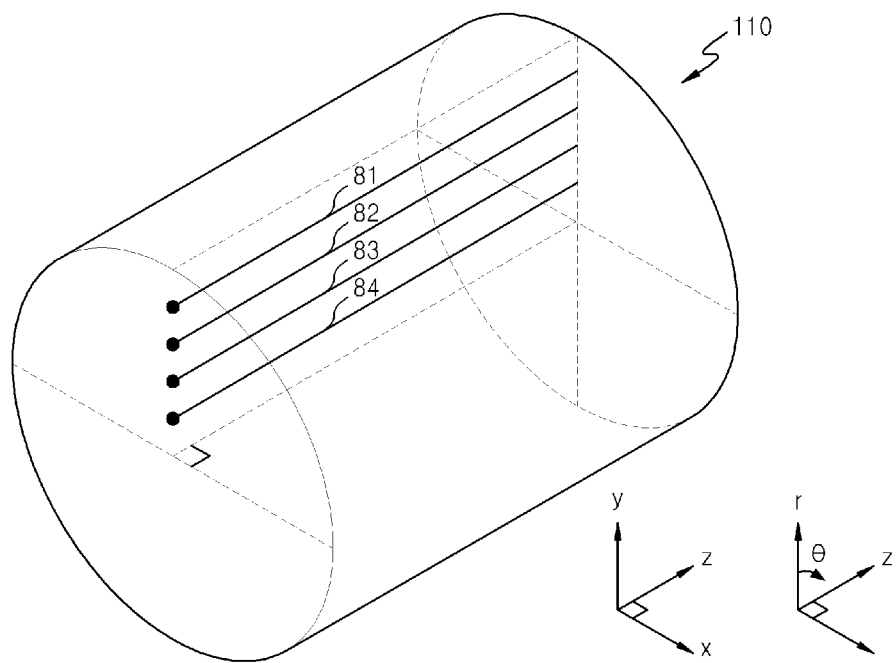
FIG. 8 is a diagram illustrating an example of changing locations of linear gamma ray sources in a detection space of a detector.

FIG. 8 is a diagram for describing an example of a method of changing locations of linear gamma ray sources in a detection space of the detector 110. Referring to FIG. 8, the control unit 41 changes the locations of the linear gamma ray sources along straight lines 81 to 84. The signal obtaining unit 42 obtains a signal emitted from each of the linear gamma ray sources according to each location during a predetermined period of time. The straight lines 81 to 84 are parallel to a z-axis. Accordingly, the linear gamma ray sources have their lengths aligned in a z-axial direction. Thus, the LSF generation unit 43 generates a straight line LSF corresponding to each location from the signal according to each location obtained from the signal obtaining unit 42. In this regard, the LSF is a function indicating a degree of spread of a line light source and corresponds to the PSF indicating a degree of spread of a point light source.

In comparison to examples in which point gamma ray sources are used as illustrated in FIG. 6, there is no longer a necessity of repetitive measurement in the z-axial direction in examples in which the linear gamma ray sources are used. For instance, in examples in which the point gamma ray sources are used, a PSF is generated with respect to 40 voxels for each x-y plane, and a PSF corresponding to the total number of 1600 voxels is generated through 40 repetitive measurements in the z-axial direction. On the other hand, in examples in which a linear gamma ray source is used, an LSF is generated with respect to 40 straight lines crossing 40 voxels on the x-y plane and simultaneously parallel to the z-axis so that the necessity of the repetitive measurement in the z-axial direction no longer exists. Therefore, in examples in which linear gamma ray sources are used, time necessary for obtaining all signals is reduced by ¹⁄₄₀ compared to examples in which point gamma ray sources are used.

Referring back to FIG. 4, the signal obtaining unit 42 obtains a signal emitted from each of the linear gamma ray sources with respect to each of the locations of the linear gamma ray sources changed by the control unit 41. For example, the signal obtaining unit 42 obtains the signal emitted from each of the linear gamma ray sources with respect to each of the locations of the linear gamma ray sources by obtaining a first signal emitted from the linear gamma ray source located at a first location and obtaining a second signal emitted from the linear gamma ray source located at a second location.

The LSF generation unit 43 generates an LSF with respect to a straight line corresponding to each location by using the signal obtained with respect to each of the changed locations. For example, the LSF generation unit 43 generates the LSF with respect to a first straight line corresponding to the first location by using the first signal obtained with respect to the first location. In this regard, since a gamma ray source is linear, a straight line that extends from the linear gamma ray source located at the first location is the first straight line corresponding to the first location. Likewise, a straight line extending from the linear gamma ray source located at the second location is the second straight line corresponding to the second location.

The separation unit 44 separates the LSF with respect to each of the straight lines into a PSF with respect to each of at least one voxel included in each straight line.

According to another example, a linear gamma ray source 81 may be generated by continuously placing gamma ray sources on a straight line as well as by discontinuously placing a plurality of point gamma ray sources on a straight line. Also, the plurality of point gamma ray sources may be regularly arranged within a uniform space.

Spaces between the plurality of point gamma ray sources influence spaces between peaks of a LSF. For example, the greater the spaces between the plurality of point gamma ray sources, the greater the spaces between the peaks of the LSF. Also, the greater the spaces between the peaks of the LSF, the more easily the separation unit 44 may detect and separate the peaks. Thus, the spaces between the plurality of point gamma ray sources may be variously set according to easy detection and separation of the peaks of the separation unit 44, accuracy required for the blur model, an arrangement space between detectors of an applicable scanner, etc.

The blur model generation unit 45 generates the blur model of the detector 110 from the PSF with respect to each of at least one voxel. For example, the blur model generation unit 45 generates the blur model of the detector 110 from the PSF with respect to the at least one voxel generated by the separation unit 44.

An example of a method of calculating a PSF with respect to some voxels and estimating a PSF with respect to other voxels from the calculated PSF is an interpolation method. The interpolation method involves estimating a PSF in a third location between a first location and a second location by giving a weight to a PSF of the first location and a PSF of the second location. In another example, in the event that different voxels have the same PSF, an operation of generating a PSF with respect to one of different voxels and generating a PSF with respect to other voxels may be omitted.

As described above, it is practically impossible to measure PSFs in all voxels. Thus, an interpolation method of measuring PSFs with respect to a first voxel and a second voxel and estimating a PSF with respect to a third voxel between the first voxel and the second voxel may be used to determine the blur model. In addition, the blur model generation unit 45 may use an interpolation method of estimating a PSF in a third location by giving a weight to a PSF of the first location and a PSF of the second location. Accordingly, the blur model generation unit 45 generates the blur model of the detector 110 from the PSF with respect to each of the at least one voxel by using the interpolation method.

For example, in the even that PSFs of the first voxel and the second voxel are identical or diagonal to each other due to a structure of a detector, and the PSF with respect one of the first and second voxels can be estimated from the PSF with respect to the other voxel, the blur model generation unit 45 may use a method of estimating the PSF with respect to the second voxel from the PSF with respect to the first voxel obtained from the separation unit 44. Accordingly, the blur model generation unit 45 generates the blur model of the detector 110 from the PSF with respect to each of the at least one voxel.

According some of examples described above, a blur model generation unit 45 may generate a blur model of a detector 110 by generating a PSF with respect to all voxels of the detector 110 from the PSF with respect to the plurality of voxels generated by the separation unit 44. Alternatively, the blur model generation unit 45 may generate the blur model of the detector 110 by generating a PSF with respect to some other voxels of the detector 110 from the PSF with respect to the plurality of voxels generated by the separation unit 44. In this case, PSF information regarding some voxels is omitted in the generated blur model. Thus, in a case where an image is generated using the blur model later, an apparatus for generating the image may obtain PSF information regarding all of the voxels of the detector 110 by estimating a PSF regarding omitted voxels from the PSF included in the blur model of the detector 110.

The blur model of a detector 110 generated by a blur model generation unit 45 may be transmitted to the storage device 500. Also, the blur model generation unit 45 may generate the blur model of the detector 110 by using the PSF with respect to the voxels of the detector 110 as a parameter as described above. In this regard, a capacity of the blur model generated by the blur model generation unit 45 is remarkably reduced as the blur model is used as the parameter.

Figure 5:
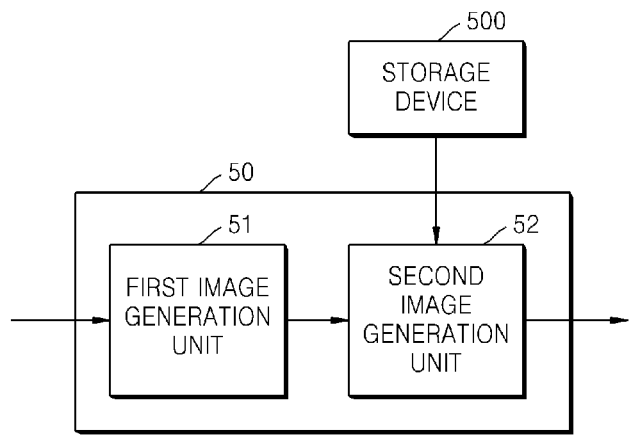
FIG. 5 is a partial block diagram illustrating another example of an apparatus for generating a medical image.

FIG. 5 is a block diagram of an example of an image generation unit 50 that generates a medical image. According to this example, the apparatus for generating the medical image of FIG. 1 may be used to generate an image of a cross-section of the body of a patient as well as to generate a blur model based on the image obtained by the detector 110. In an example in which the apparatus for generating the medical image of FIG. 1 is used to generate an image of a cross-section of a patient, the computer 200 of FIG. 1 may include an image generation unit 50. The image generation unit 50 may include one or more processors.

Referring to FIG. 5, an example of an image generation unit 50 includes a first image generation unit 51 and a second image generation unit 52. The second image generation unit 52 may generate a second image by obtaining a blur model from the storage device 500. Alternatively, the second image generation unit 52 may generate the second image by obtaining a blur model used as a parameter from the storage device 500.

The first image generation unit 51 generates a first image with respect to a target by detecting a signal emitted from a tracer injected into the target. For example, the signal detection device 100 of FIG. 1 may detect two gamma rays emitted by combining a positron emitted from the tracer injected into a body of the patient with electrons. The signal detection device 100 may transmit LOR data regarding the detected gamma rays to the computer 200. The first image generation unit 51 may obtain the signal from the signal detection device 100, estimate a location of the tracer from the obtained signal, and generate the first image with respect to the target indicating the location of the tracer in the target based on the estimated location.

The second image generation unit 52 may generate the second image by applying the blur model to the first image generated by the first image generation unit 51. For example, the second image generation unit 52 may generate the second image by applying a blur model of the detector 110 obtained from the storage device 500 to the first image generated by the first image generation unit 51. The blur model stored in the storage device 500 may be the blur model generated by the blur model generation device 40 illustrated in FIG. 4.

Accordingly, the first image may be a low resolution blurry image, and the second image may be a high resolution image from which the blurring present in the first image has been eliminated by applying the blur model of the detector 110.

For example, the second image generation unit 52 may generate the second image using an expectation maximization (EM) algorithm. The EM algorithm is used to precisely approach a high resolution image through a repetitive calculation according to equation 1 below.

$$n_j^{k+1} = \frac{n_j^k}{\sum_i a_{ij}} \sum_i^I a_{ij} \frac{m_i}{q_i^k}$$ <Equation 1>

In Equation 1 above, j denotes a voxel coordinate indicating a location in the detector 110, i denotes a type of LOR data, and k denotes a number of repeated algorithms. Accordingly, $n_j^k$ of Equation 1 denotes a pixel output value with respect to the voxel j in the detector 110, and $a_{ij}$ denotes a value indicating a probability of detecting the LOR i when a gamma ray is emitted from the voxel j, and may be calculated from the blur model. $m_i$ denotes a number of the detected LOR i, and $q_i^k$ is calculated from $a_{ij}$ and $n_j^k$ according to Equation 2 below.

$$q_i^k = \sum_j^I a_{ij} n_j^k$$ <Equation 2>

Figure 9:
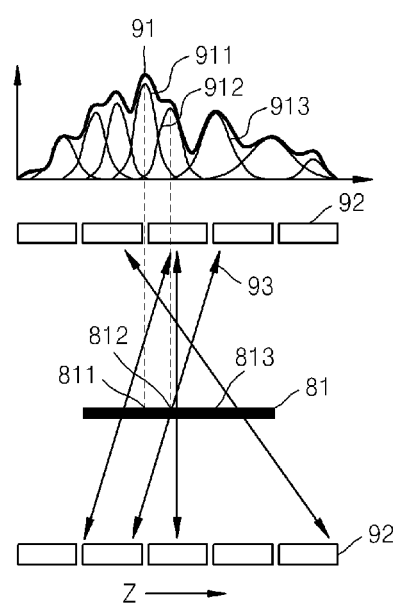
FIG. 9 is a diagram illustrating an example of separating a line spread function (LSF) into a point spread function (PSF), which may be performed by a separation unit illustrated in FIG. 4.

The EM algorithm and the method of applying the blur model are known to one of ordinary skill in the art.
FIG. 9

Figure 10:
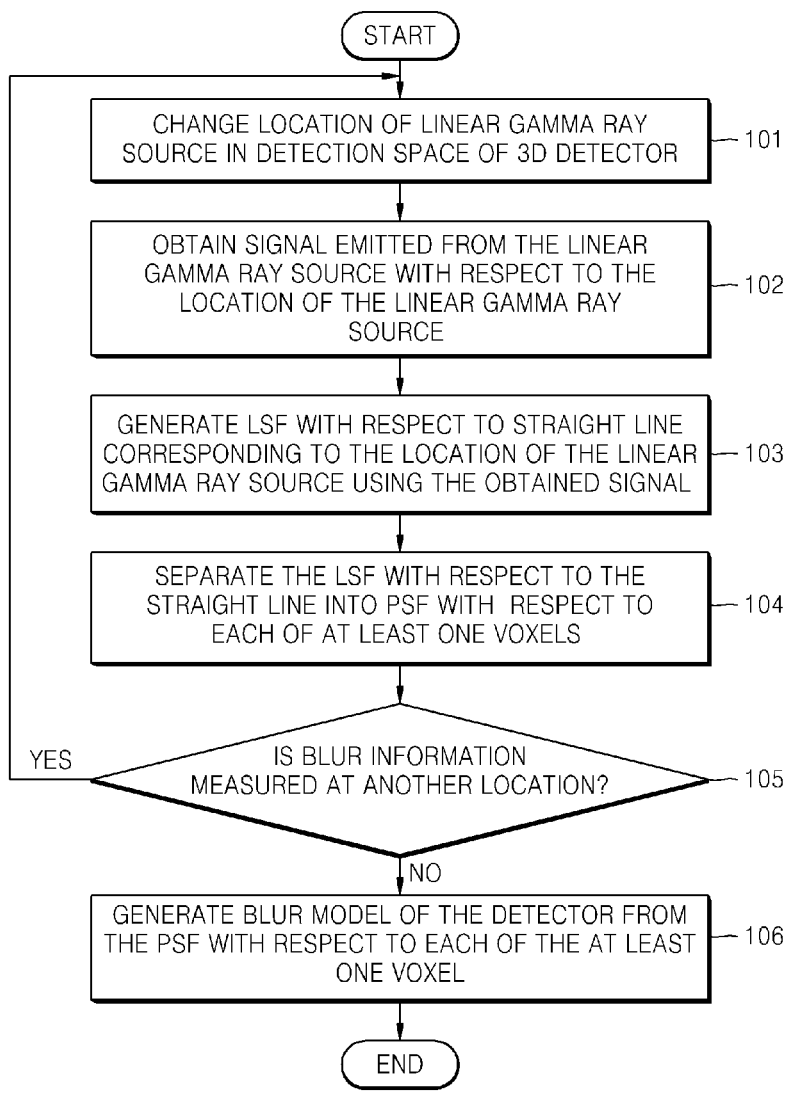
FIG. 10 is a flowchart illustrating an example of a blur model generating method.

FIG. 10 is a flowchart illustrating an example of a blur model generating method. Referring to FIG. 10, in operation 101, the control unit 41 changes a location of a linear gamma ray source in a detection space of a 3D detector. In operation 102, the signal obtaining unit 42 obtains a signal emitted from the linear gamma ray source for a predetermined period of time with respect to the location of the linear gamma ray source changed by the control unit 41. In operation 103, the LS generation unit 43 generates a LSF with respect to a straight line corresponding to the location at which each signal is obtained by fitting the signal obtained by the signal obtaining unit 42. In operation 104, the separation unit 44 separates the LSF with respect to the straight line generated by the LSF generation unit 43 into a PSF with respect to each of at least one voxel included in the straight line.

In operation 105, the blur model generation device 40 determines whether to measure blur information at another location. If the blur model generation device 40 determines that it is necessary to measure the blur information at another location, operation 101 is performed. If the blur model generation device 40 determines it is not necessary to measure the blur information at another location, operation 106 is performed. In operation 106, the blur model generation device 45 generates a blur model of the detector 110 from the PSF with respect to each of the at least one voxel generated by the separation unit 44.

Figure 11:
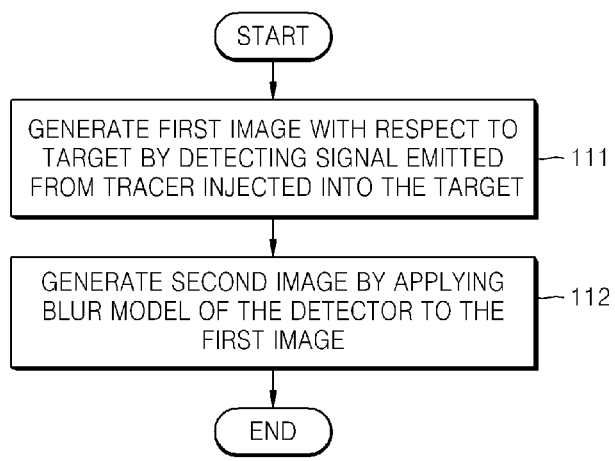
FIG. 11 is a flowchart illustrating an example of a medical image generating method.

FIG. 11 is a flowchart illustrating an example of a medical image generating method. Referring to FIG. 11, in operation 111, the first image generation unit 51 generates a first image with respect to a target by detecting a signal emitted from a tracer injected into the target. In operation 112, the second image generation unit 52 generates a second image by applying a blur model of the detector 110 to the first image generated by the first image generation unit 51. In this regard, the blur model may be the blur model of the detector 110 generated by using the blur model generating method explained with respect to FIG. 10.

According to the examples described above, a method of generating an image of a target through the PET may generate a high resolution image by generating a blur model of the detector 110 and applying the blur model to an image obtained by an image generation device. The blur model may be generated by a method of generating a PSF of voxels by using a point gamma ray source.

According to some of the examples described above, a linear gamma ray source may be used to separate an LSF measured from the linear gamma ray source and to generate a PSF with respect to a plurality of voxels disposed in a location of the linear gamma ray source. Accordingly, in this example, there may be no longer a necessity of repeating an operation of moving the point gamma ray source in a straight line direction and generating a PSF. For example, in the event that the linear gamma ray source is disposed parallel to a z-axial direction, the necessity of repeating an operation of moving the point gamma ray source in the z-axial direction and generating the PSF no longer exists. Therefore, it takes less time to generate the blur model. Accordingly, the blur model may be generated quickly.

For example, if 40 repetitive measurements are conventionally performed by moving the point gamma ray source in an axial direction, in the case of using the point gamma ray source, the total measurement time is reduced by 1/40 compared to the case of using the point gamma ray source. Because the generation of the blur model takes processing time, the conventional blur model of a detector is generated before the product release, and the product is sold after the blur models is stored in a memory of a medical imaging apparatus. However, a time taken to measure the blur model is reduced by using the linear gamma ray source. Thus, when a linear gamma ray source is used, after a product is sold, a user may newly update the blur model of the detector.

Also, the user may change the previously-set spacing between locations of gamma line sources, change the previously-set spacing between the point gamma ray sources included in linear gamma ray sources, or use the user input device 400 to input another adjustment factor when setting the locations of gamma line sources. Thus, an image and a blur model having quality desired by the user may be generated in a tradeoff relationship between the quality of the image and blur model and an arithmetic load or arithmetic time of a processor.

According to one or more of examples described above, a blur model may be generated with respect to a detector of a medical imaging apparatus by using a linear gamma ray source, and a high resolution medical image may be generated using the generated blur model to refine the obtained image.

The above-described examples of blur model generating methods according to FIG. 10 and the medical image generating methods according to FIG. 11 may be written as computer programs and may be implemented in general-use digital computers that execute programs using a non-transitory computer readable recording medium. Examples of non-transitory computer readable recording medium that may be used to store such programs include, but not limited to, magnetic storage media such as ROMs, floppy disks, hard disks, and the like, and optical recording media such as CD-ROMs, DVDs, and the like.

Also described above are examples of methods of generating a blur model of a detector of a medical imaging apparatus that may be used to generate a medical image. Such a method may involve: changing locations of linear gamma ray sources in a detection space of the detector and obtaining signals emitted from the linear gamma ray sources with respect to the changed locations; generating a line spread function (LSF) with respect to each of straight lines corresponding to each of the locations by using the obtained signal with respect to each of the locations; separating the LSF with respect to each of the straight lines into a point spread function (PSF) with respect to each of at least one voxel included in each of the straight lines; and generating a blur model of the detector from the PSF with respect to each of the at least one voxel.

The linear gamma ray sources may comprise a plurality of point gamma ray sources. The plurality of point gamma ray sources may be spaced apart from each other by a uniform space.

In this example, the separating may involve fitting the LSF with respect to each of the straight lines to a sum of a plurality of functions. Each of the plurality of functions may be the PSF with respect to each of the at least one voxel. The plurality of functions may be Gaussian functions.

The method may further involve: calculating a parameter for representing a function corresponding to the separated PSF. The blur model of the detector may be generated from a parameter with respect to the at least one voxel. In this example, there may be at least two linear gamma ray sources that are disposed parallel to each other.

Also described above are examples of methods of generating a high resolution medical image. Such a method may involve: changing locations of linear gamma ray sources in a detection space of the detector and obtaining signals emitted from the linear gamma ray sources with respect to the changed locations; generating a line spread function (LSF) with respect to each of straight lines corresponding to each of the locations by using the obtained signal with respect to each of the locations; separating the LSF with respect to each of the straight lines into a point spread function (PSF) with respect to each of at least one voxel included in each of the straight lines; generating a blur model of the detector from the PSF with respect to each of the at least one voxel; generating a first image with respect to a target by detecting a signal emitted from a tracer injected into the target; and generating a second image by applying the blur model to the first image.

In such a method, a resolution of the second image may be higher than that of the first image. In such a method, the generating of the second image may comprise: using an expectation maximization (EM) algorithm.

Also described above are examples of apparatuses for generating a blur model of a detector of a medical imaging apparatus that is used for generating a medical image. Such an apparatus may include: a signal obtaining unit for changing locations of linear gamma ray sources in a detection space of the detector and obtaining signals emitted from the linear gamma ray sources with respect to the changed locations; an LSF generation unit for generating a LSF with respect to each of straight lines corresponding to each of the locations by using the obtained signal with respect to each of the locations; a separation unit for separating the LSF with respect to each of the straight lines into a PSF with respect to each of at least one voxel included in each of the straight lines; and a blur model generation unit for generating a blur model of the detector from the PSF with respect to each of the at least one voxel.

In such an apparatus, the linear gamma ray sources may comprise a plurality of point gamma ray sources. The plurality of point gamma ray sources may be spaced apart from each other by a uniform space. The separation unit may comprise a fitting unit for fitting the LSF with respect to each of the straight lines to a sum of a plurality of functions, and each of the plurality of functions may be the PSF with respect to each of the at least one voxel. The plurality of functions may be Gaussian functions.

Such an apparatus may further include: a parameter calculation unit for calculating a parameter for representing a function corresponding to the separated PSF, and the blur model generation unit may generate the blur model of the detector from a parameter with respect to the at least one voxel.

Such an apparatus may include at least two linear gamma ray sources that are disposed parallel to each other.

Also described above are examples of apparatuses for generating a high resolution medical image. Such an apparatus may include: a signal obtaining unit for changing locations of linear gamma ray sources in a detection space of the detector and obtaining signals emitted from the linear gamma ray sources with respect to the changed locations; an LSF generation unit for generating a LSF with respect to each of straight lines corresponding to each of the locations by using the obtained signal with respect to each of the locations; a separation unit for separating the LSF with respect to each of the straight lines into a PSF with respect to each of at least one voxel included in each of the straight lines; a blur model generation unit for generating a blur model of the detector from the PSF with respect to each of the at least one voxel; a first image generation unit for generating a first image with respect to a target by detecting a signal emitted from a tracer injected into the target; and a second image generation unit for generating a second image by applying the blur model to the first image.

The second image generation unit may use an EM algorithm to generate the second image.

Also described above is a non-transitory computer-readable recording medium having recorded thereon a program for executing methods described above.

The units described herein may be implemented using a hardware component, a software component, or a combination of both. For example, the units may include a processing device and memory storage. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of generating a blur model of a detector, the method comprising:
changing locations of linear gamma ray sources along at least one line and obtaining signals emitted from the linear gamma ray sources;
obtaining a point spread function (PSF) with respect to at least one voxel included in the at least one line; and
generating a blur model of the detector from the PSF.

2. The method of claim 1, wherein the obtaining of the PSF with respect to the at least one voxel comprises:
generating a line spread function (LSF) with respect to the at least one line based on the obtained signals; and
separating the LSF with respect to each of the at least one line into the PSF with respect to each of the at least one voxel.

3. The method of claim 1, wherein the linear gamma ray sources comprise a plurality of point gamma ray sources.

4. The method of claim 3, wherein the plurality of point gamma ray sources are spaced apart from each other by a uniform space.

5. The method of claim 2, wherein the separating comprises fitting the LSF with respect to each of the at least one line to a sum of a plurality of functions,
wherein each of the plurality of functions is the PSF with respect to each of the at least one voxel.

6. The method of claim 5, wherein the plurality of functions are Gaussian functions.

7. The method of claim 5, further comprising:
calculating a parameter for representing a function corresponding to the separated PSF,
wherein the blur model of the detector is generated from the parameter with respect to the at least one voxel.

8. The method of claim 1, wherein the linear gamma ray sources comprise at least two linear gamma ray sources that are disposed parallel to each other.

9. A method of generating a medical image, the method comprising:
changing locations of linear gamma ray sources along at least one line and obtaining signals emitted from the linear gamma ray sources;
obtaining a point spread function (PSF) with respect to at least one voxel included in the at least one line;
generating a blur model of the detector from the PSF;
generating a first image based on a signal emitted from a tracer; and
generating a second image by applying the blur model to the first image.

10. The method of claim 9, wherein the obtaining of the PSF with respect to the at least one voxel comprises:
generating a line spread function (LSF) with respect to the at least one line based on the obtained signals; and
separating the LSF with respect to each of the at least one line into the PSF with respect to each of the at least one voxel.

11. The method of claim 9, wherein a resolution of the second image is higher than that of the first image.

12. The method of claim 9, wherein the generating of the second image comprises:
using an expectation maximization (EM) algorithm.

13. An apparatus for generating a blur model, the apparatus comprising:
a signal obtaining unit configured to change locations of linear gamma ray sources along a line and obtaining signals emitted from the linear gamma ray sources;
a PSF obtaining unit configured to obtain a point spread function (PSF) with respect to at least one voxel included in the at least one line; and
a blur model generation unit configured to generate a blur model from the PSF.

14. The apparatus of claim 13, wherein the PSF obtaining unit comprises:
a line spread function (LSF) generation unit configured to generate a LSF with respect to the least one line based on the obtained signals; and
a separation unit for separating the LSF with respect to each of the at least one line into the PSF with respect to each of the at least one voxel.

15. The apparatus of claim 13, wherein the linear gamma ray sources comprise a plurality of point gamma ray sources.

16. The apparatus of claim 15, wherein the plurality of point gamma ray sources are spaced apart from each other by a uniform space.

17. The apparatus of claim 14, wherein the separation unit comprises a fitting unit for fitting the LSF with respect to each of the at least one line to a sum of a plurality of functions,
wherein each of the plurality of functions is the PSF with respect to each of the at least one voxel.

18. The apparatus of claim 17, wherein the plurality of functions are Gaussian functions.

19. The apparatus of claim 17, further comprising:
a parameter calculation unit for calculating a parameter for representing a function corresponding to the separated PSF,
wherein the blur model generation unit is configured to generate the blur model from the parameter with respect to the at least one voxel.

20. The apparatus of claim 13, wherein the linear gamma ray sources comprise at least two linear gamma ray sources that are disposed parallel to each other.

21. An apparatus for generating a medical image, the apparatus comprising:
a signal obtaining unit configured to change locations of linear gamma ray sources along at least one line and obtaining signals emitted from the linear gamma ray sources;
a point spread function (PSF) obtaining unit configured to obtain a PSF with respect to at least one voxel included in the at least one line;
a blur model generation unit configured to generate a blur model from the PSF;
a first image generation unit configured to generate a first image based on a signal emitted from a tracer; and
a second image generation unit configured to generate a second image by applying the blur model to the first image.

22. The apparatus of claim 21, wherein the PSF obtaining unit comprises:
a line spread function (LSF) generation unit configured to generate a LSF with respect to the least one line based on the obtained signals; and
a separation unit for separating the LSF with respect to each of the at least one line into the PSF with respect to each of the at least one voxel.

23. The apparatus of claim 21, wherein the second image generation unit uses an expectation maximization (EM) algorithm to generate the second image.

24. A non-transitory computer-readable recording medium having recorded thereon a program for executing the method of claim 1.

* * * * *